US010627894B2

United States Patent
Ahn

(10) Patent No.: US 10,627,894 B2
(45) Date of Patent: Apr. 21, 2020

(54) ELECTRIC DEVICE CONTROL APPARATUS, AND ELECTRIC DEVICE CONTROL METHOD USING SAME

(71) Applicant: REXGEN, Jeonju-si, Jeollabuk-do (KR)

(72) Inventor: Soon Hyun Ahn, Anyang-si (KR)

(73) Assignee: REXGEN, Jeonju-si, Jeollabuk-do (KR)

( * ) Notice: Subject to any disclaimer, the term of this patent is extended or adjusted under 35 U.S.C. 154(b) by 115 days.

(21) Appl. No.: 15/529,977

(22) PCT Filed: Jul. 13, 2016

(86) PCT No.: PCT/KR2016/007627
§ 371 (c)(1),
(2) Date: May 25, 2017

(87) PCT Pub. No.: WO2017/082514
PCT Pub. Date: May 18, 2017

(65) Prior Publication Data
US 2017/0322618 A1     Nov. 9, 2017

(30) Foreign Application Priority Data
Nov. 12, 2015    (KR) ........................ 10-2015-0159117

(51) Int. Cl.
*G06F 3/01*      (2006.01)
*G06F 1/3296*      (2019.01)
(Continued)

(52) U.S. Cl.
CPC .......... *G06F 1/3296* (2013.01); *G06F 1/3209* (2013.01); *G06F 3/01* (2013.01);
(Continued)

(58) Field of Classification Search
CPC ........ G06F 1/3296; G06F 1/3209; G06F 3/01; G06F 3/147; H02J 13/0075; H02J 2310/14
(Continued)

(56) References Cited

U.S. PATENT DOCUMENTS 8,782,455 B2 *   7/2014   Fukada ................. G06F 1/3209
                                                          713/323
2010/0033424 A1 *   2/2010   Kabasawa ............. G01C 17/28
                                                          345/156
(Continued)

FOREIGN PATENT DOCUMENTS

KR    10-2013-0128744 A    11/2013
KR    10-2014-0118347 A    10/2014
(Continued)

OTHER PUBLICATIONS

Brought to you by Visible Energy, UFO Power Center, 2011 (Year: 2011).*
(Continued)

*Primary Examiner* — Aurel Prifti
(74) *Attorney, Agent, or Firm* — Revolution IP, PLLC

(57) ABSTRACT

An electrical appliance control device for controlling power supplied to an electrical appliance, comprises: an output unit configured to output a predetermined event for each predetermined period during an operation mode; a determination unit configured to determine whether predetermined information is inputted by a user in response to the predetermined event; and a control unit configured to control power supplied to the electrical appliance corresponding to whether the predetermined information is inputted.

18 Claims, 3 Drawing Sheets

(51) Int. Cl.
| | |
|---|---|
| *H02J 13/00* | (2006.01) |
| *H02J 9/00* | (2006.01) |
| *G06F 1/3209* | (2019.01) |
| *G06F 3/147* | (2006.01) |
| *A61M 21/00* | (2006.01) |
| *A61M 21/02* | (2006.01) |
| *A61B 5/00* | (2006.01) |
| *H02J 3/14* | (2006.01) |

(52) U.S. Cl.
CPC ............. *G06F 3/147* (2013.01); *H02J 9/005* (2013.01); *H02J 13/0075* (2013.01); *A61B 5/681* (2013.01); *A61M 21/02* (2013.01); *A61M 2021/0044* (2013.01); *A61M 2205/332* (2013.01); *A61M 2205/3306* (2013.01); *A61M 2205/3368* (2013.01); *A61M 2205/3569* (2013.01); *A61M 2205/3592* (2013.01); *A61M 2205/505* (2013.01); *A61M 2230/00* (2013.01); *A61M 2230/63* (2013.01); *H02J 3/14* (2013.01); *H02J 2310/14* (2020.01); *Y02B 70/3233* (2013.01); *Y02B 70/3266* (2013.01); *Y02B 90/2653* (2013.01); *Y04S 20/225* (2013.01); *Y04S 20/242* (2013.01); *Y04S 40/126* (2013.01)

(58) Field of Classification Search
USPC .................. 713/300, 323, 324, 193; 307/140
See application file for complete search history.

(56) References Cited

U.S. PATENT DOCUMENTS

| | | | | |
|---|---|---|---|---|
| 2012/0278640 | A1* | 11/2012 | Caglianone | G06F 1/3231 713/323 |
| 2013/0339766 | A1* | 12/2013 | Chen | G06F 1/266 713/300 |
| 2014/0089702 | A1* | 3/2014 | Gupta | G06F 1/32 713/323 |
| 2015/0067375 | A1* | 3/2015 | Iwasa | G06F 1/266 713/324 |
| 2015/0137621 | A1* | 5/2015 | Emby | G05B 11/01 307/140 |
| 2015/0221278 | A1* | 8/2015 | Le Grand | G06F 1/3265 345/156 |
| 2016/0124477 | A1* | 5/2016 | Guy | H04L 12/10 713/300 |
| 2016/0124868 | A1* | 5/2016 | Logue | H04L 63/0428 713/193 |
| 2016/0179179 | A1* | 6/2016 | An | G06F 1/3265 345/212 |
| 2017/0127354 | A1* | 5/2017 | Garland | H04B 1/385 |
| 2017/0131332 | A1* | 5/2017 | Gelonese | G01R 22/063 |
| 2018/0054587 | A1* | 2/2018 | Haskey | G05B 15/02 |
| 2018/0143677 | A1* | 5/2018 | Gelonese | G06F 1/32 |

FOREIGN PATENT DOCUMENTS

| | | | | |
|---|---|---|---|---|
| KR | 10-1460225 B1 | 11/2014 | | |
| KR | 10-2015-0098098 A | 8/2015 | | |
| KR | 10-1546226 B1 | 8/2015 | | |
| WO | WO-2015103668 A1 * | 7/2015 | ............. | G06F 1/266 |
| WO | WO-2016081982 A1 * | 6/2016 | ............. | G01D 4/002 |
| WO | WO-2016115589 A1 * | 7/2016 | ........... | H01R 25/003 |

OTHER PUBLICATIONS

International Search Report for PCT/KR2016/007627 dated Oct. 6, 2016 from Korean Intellectual Property Office.

* cited by examiner

【Figure 1】
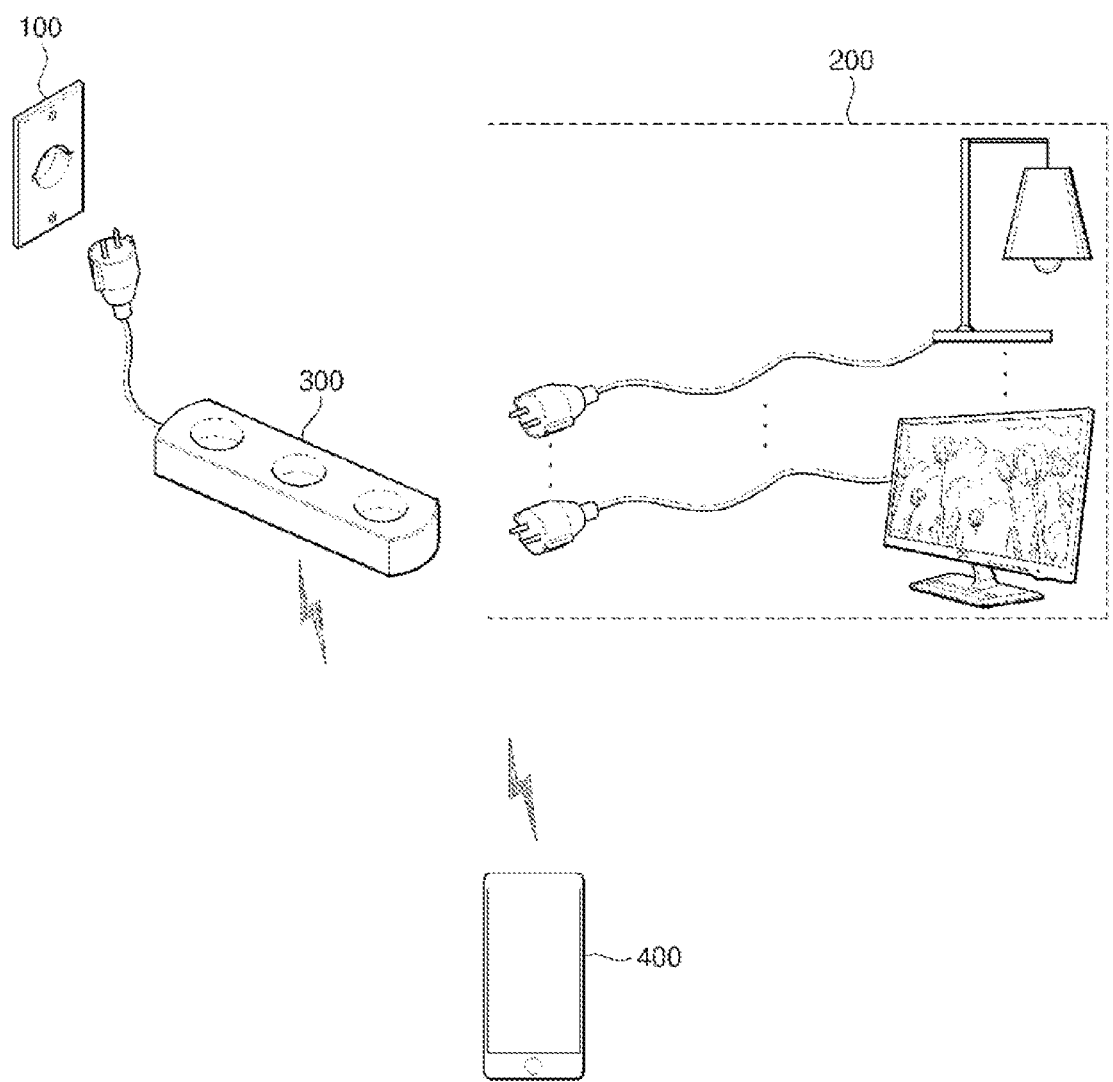

[Figure 2]
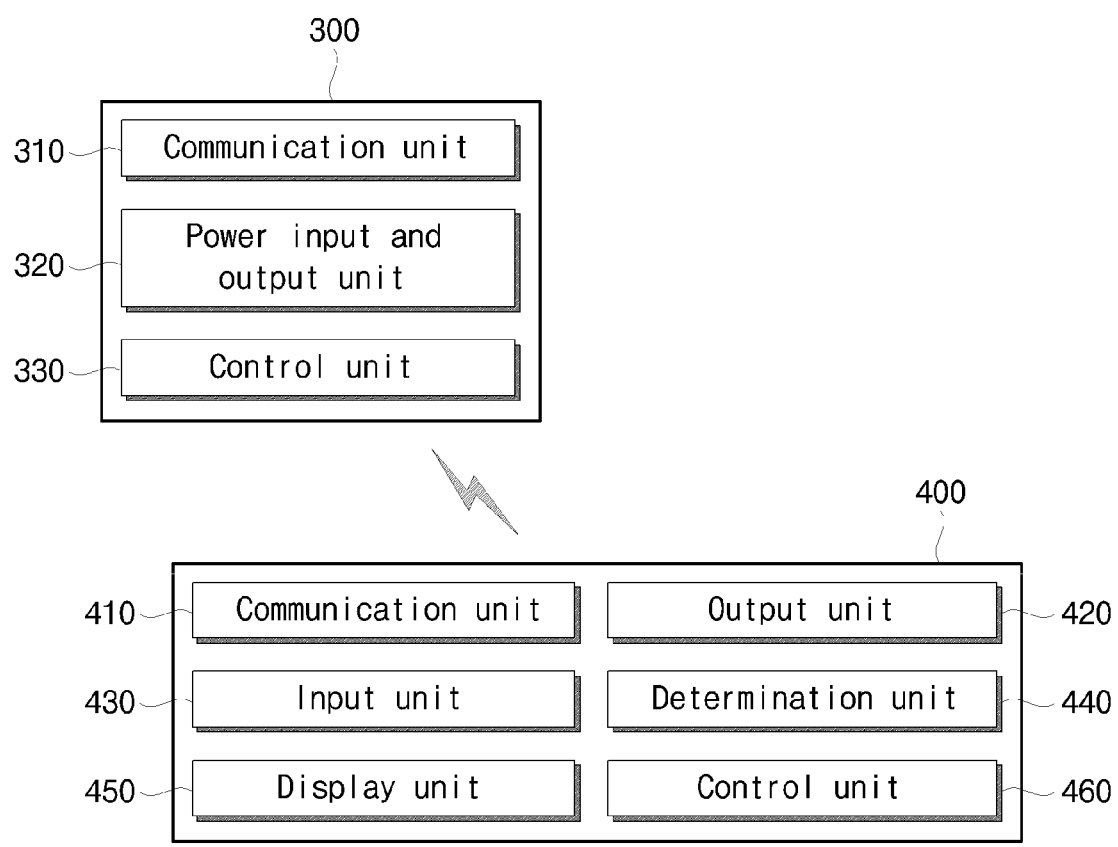

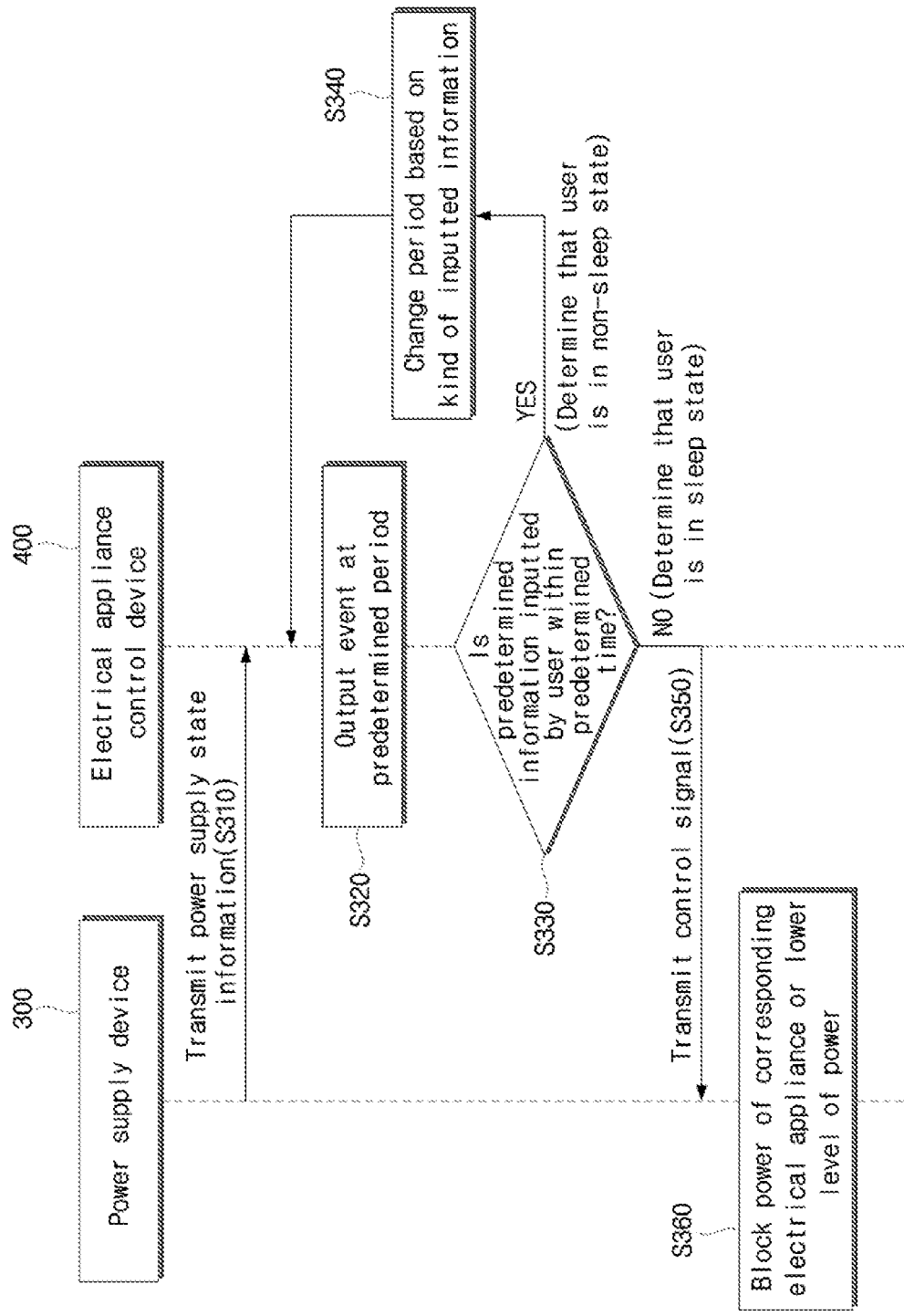
[Figure 3]

ELECTRIC DEVICE CONTROL APPARATUS, AND ELECTRIC DEVICE CONTROL METHOD USING SAME

CROSS REFERENCE TO PRIOR APPLICATIONS

This application is a National Stage Application of PCT International Patent Application No. PCT/KR2016/007627 filed on Jul. 13, 2016, under 35 U.S.C. § 371, which claims priority to Korean Patent Application No. 10-2015-0159117 filed on Nov. 12, 2015, which are all hereby incorporated by reference in their entirety.

TECHNICAL FIELD

The present invention relates to a device and method for controlling an electrical appliance, and more particularly, to a device and method for controlling an electrical appliance that may control power supplied to the electrical device based on information of a user state.

BACKGROUND ART

Many people enjoy reading, listening to music, or watching movies before sleeping. However, while reading, listening to music, or watching movies, they often fall asleep without turning off electrical appliances such an electric light, a TV, and the like.

When they fall asleep without turning off the electrical appliances, since their bodies are in a tense state due to electromagnetic waves, heat, light, or the like generated in the electrical appliance, they cannot sleep well enough, and electricity charges are increased due to long use of electrical appliances.

In order to solve these problems, a method for controlling the electrical appliances through a remote control unit has been developed. Generally, the remote control unit transmits a control command to an electrical appliance through infrared communication, and the electrical appliance performs an operation corresponding to the control command. However, the control method of using the remote control unit needs to operate buttons of the remote control unit, and when the user sleeps without operating the remote control, the electrical appliance can be controlled.

In addition, a method of controlling power supply of an electrical appliance by determining whether a user is sleeping based on motion information of a user received to a user terminal from a smart band that can be mounted on a user's body, has been proposed. However, for the control method of using the smart band, the user must wear the smart band, and when the user does not move for a predetermined period of time in a state in which the user is not sleeping, since it is determined that the user is in the sleep state, the electrical appliance may be powered off.

DISCLOSURE

Technical Problem

The present invention has been made in an effort to provide a device and method for controlling an electrical appliance that may control power supplied to the electrical device based on information of a user state.

Technical Solution

An exemplary embodiment of the present invention provides an electrical appliance control device for controlling power supplied to an electrical appliance, including: an output unit configured to output a predetermined event for each predetermined period during an operation mode; a determination unit configured to determine whether predetermined information is inputted by a user in response to the predetermined event; and a control unit configured to control power supplied to the electrical appliance corresponding to whether the predetermined information is inputted.

The determination unit may determine a state of the user based on whether the predetermined information is inputted, and the control unit may control the power supplied to the electrical appliance by maintaining the operation mode or switching the operation mode to a standby mode corresponding to the state of the user.

The determination unit may determine that the user is in a non-sleep state when the predetermined information is inputted within a predetermined time from when the predetermined event is outputted, and the determination unit may determine that the user is in a sleep state when the predetermined information is not inputted within a predetermined time from when the predetermined event is outputted.

When the user is in the non-sleep state, the control unit may maintain the operation mode, and may initialize a start counting time of the predetermined period.

When the operation mode is maintained, the control unit may update a period of an event outputted for a next period to a period corresponding to a kind of the predetermined information inputted by the user.

The electrical appliance control device may further include an input unit configured to receive the predetermined information and to provide it to the determination unit, wherein the predetermined information may include at least one of sound information, vibration information, and touch information inputted by the user corresponding to the predetermined event, and the predetermined event may include at least one of a sound event, a vibration event, a light event, and a screen popup event.

The electrical appliance control device may include a communication unit communicating with a power supply device that manages the power supplied to the electrical appliance, and the control unit may transmit a control signal for controlling the power supplied to the electrical appliance to the power supply device through the communication unit.

The power supply device may include at least one socket outlet that controls power supplied to at least one electrical appliance, and the control signal may include information of maintaining or blocking the power supplied to the electrical appliance, or of changing a level of the power, which is power management information applied to the standby mode as a mode that is switchable in the operation mode corresponding to whether the predetermined information is inputted.

The electrical appliance control device may further include a display unit that receives a list of the electrical appliances corresponding to a specific code of each socket outlet from the power supply device and state information of power supplied to the electrical appliances to display them on a screen.

The electrical appliance control device may include a communication unit that wirelessly communicates with a user terminal, and the control unit may receive the predetermined information from the user terminal through the communication unit to provide it to the determination unit, and may provide the state information of the power supplied to the electrical appliance to the user terminal.

Another embodiment of the present invention provides an electrical appliance control method of using an electrical appliance control device for controlling power supplied to an electrical appliance, including: outputting a predetermined event for each predetermined period during an operation mode; determining whether predetermined information is inputted by a user in response to the predetermined event; and controlling power supplied to the electrical appliance corresponding to whether the predetermined information is inputted.

Advantageous Effects

According to the embodiment of the present invention, it is possible to control power supplied to an electrical appliance by determining a state of a user depending on whether or not predetermined information is inputted from the user in response to an outputted event, and thus, even when the user is sleeping while reading, watching a movie, or listening to music, the electrical appliance may be efficiently powered off or a power level thereof may be lowered.

In addition, according to the embodiment of the present invention, the user may sleep well enough without worrying about power-off of the electrical appliance and does not have to worry about electric charge caused by operation of the electrical appliance during a sleeping time.

DESCRIPTION OF THE DRAWINGS

FIG. 1 illustrates a schematic view of an electrical appliance control system according to an exemplary embodiment of the present invention.

FIG. 2 illustrates a detailed block diagram of an electrical appliance control device and a power supply device of FIG. 1.

FIG. 3 illustrates a flowchart of an electrical appliance control method performed by the electrical appliance control device of FIG. 1.

MODE FOR INVENTION

The present invention will be described more fully hereinafter with reference to the accompanying drawings, in which exemplary embodiments of the invention are shown.

FIG. 1 illustrates a schematic view of an electrical appliance control system according to an exemplary embodiment of the present invention, and FIG. 2 illustrates a detailed block diagram of an electrical appliance control device and a power supply device of FIG. 1.

As shown in FIG. 1 and FIG. 2, an electrical appliance control system according to an exemplary embodiment of the present invention includes a power supply source 100, electrical appliances 200, a power supply device 300 and an electrical appliance control device 400.

The power supply source 100 includes a socket outlet, and provides electricity supplied from the power supply source (e.g., Korea Electric Power Corporation, etc.).

The electrical appliances 200 include at least one appliance that operates by the supplied electricity, such as a lamp appliance (a fluorescent light, an electric light, etc.), an electrical appliance (a refrigerator, a television, etc.), etc.

The power supply device 300 is connected to the power supply source 100, and controls power respectively supplied to the electrical appliances 200 depending on control of the electrical appliance control device 400.

In the exemplary embodiment of the present invention, the power supply source 100 and the power supply device 300 are separately described, but the power supply device 300 and the power supply source 100 may be integrated in one to directly receive electricity from a power supply source and then to provide it to the electrical appliances 200.

The power supply device 300 includes a communication unit 310, a power input and output unit 320, and a control unit 330.

The communication unit 310 transmits and receives data to and from the electrical appliance control device 400. In this case, the communication unit 310 performs short-range wireless communication with the electrical appliance control device 400, and is preferably configured as a small module such a Bluetooth module, a Zigbee module, a Wi-fi module, and the like.

The power input and output unit 320 includes at least one plug corresponding to the socket outlet of the power supply source 100 and at least one socket outlet for supplying power to at least one electrical appliance 200, and supplies electricity inputted from the power supply source 100 to the electrical appliances 200 under the control of the control unit 330.

Alternatively, the power input and output unit 320 may include a wireless power transmission module for wireless power transmission to wirelessly supply electricity to the electrical appliances 200.

The control unit 330 controls the communication unit 310 and the power input and output unit 320, communicates with the electrical appliance control device 400 through the communication unit 310, and generates state information of power supplied to the electrical appliances 200 to transmit it to the electrical appliance control device 400.

In this case, the state information of power supplied to the electrical appliances includes state information (e.g., supplying, blocking, supply level, etc.) of power supplied to each electrical appliance 200 of each socket outlet.

In addition, the control unit 330 receives a control signal of the electrical appliance control device 400 to control (supply, block, level up, or level down) the power supply of the power input and output unit 320.

Hereinafter, referring to FIG. 2, the electrical appliance control device 400 of the present invention, which includes a communication unit 410, an output unit 420, an input unit 430, a determination unit 440, a display unit 450, and a control unit 460, will be described.

The communication unit 410 wirelessly transmits and receives data to and from at least one power supply device 300. In this case, the communication unit 410 preferably operates in a communication scheme corresponding to the communication unit 310 of the power supply device 300.

While performing an operation mode by the control unit 460, the output unit 420 outputs a predetermined event at each predetermined period. For example, the output unit 420 generates and outputs a predetermined event to the electrical appliance control device 400 at each 10 minute period. Alternatively, the output unit 420 may randomly generate and output the predetermined event when the period is set to be random.

Here, the predetermined event may correspond to at least one of a sound signal, a vibration signal, a light signal, and a screen pop-up window as an alarm signal that may be recognized by a user in the vicinity of the electrical appliance control device 400.

The input unit 430 receives predetermined information from the user corresponding to the outputted predetermined event, and provides the predetermined information to the determination unit 440. Here, the predetermined information may correspond to at least one of sound information (e.g., user's voice information), vibration information (e.g., vibration information due to shaking of the electrical appliance control device 400), and screen touch information (e.g., simple screen touch information and touch information within a predetermined area) which correspond to a response signal inputted from a user who recognizes the outputted predetermined event.

The determination unit 440 determines a state of the user based on whether the predetermined information is inputted by the user in response to the predetermined event. Here, the state of the user may mean whether the user is sleeping or not sleeping.

Specifically, when the predetermined information is inputted within a predetermined time (e.g., 1 minute) from the time at which the predetermined event is outputted, the determination unit 440 determines that the user is in a non-sleep state, and when the predetermined information is not inputted within the predetermined time, the determination unit 440 determines that the user is in a sleep state, and the determination unit 440 provides the determined result to the control unit 460.

The display unit 450 provides information that the communication unit 410 receives from the power supply device 300 on a screen. The display unit 450 may provide a list of the electrical appliances corresponding to specific codes of the respective socket outlets and the power supply state information of the electrical appliances, and may provide various convenience functions associated with the power supply control. The control unit 460 controls flows of data of respective units (410, 420, 430, 440, and 450).

The control unit 460 maintains an operation mode currently being performed in response to the state of the user determined by the determination unit 440, or switches the operation mode to a standby mode to transmit a control signal for managing the power supplied to the electrical appliances 200 to the power supply device 300.

Specifically, when the determination unit 440 determines that the user is not sleeping, the control unit 460 maintains the current operation mode. The control unit 460 initializes a start counting time of the event generation period when a response of the user exists such that the operation mode is maintained within a predetermined time (e.g., 1 minute) after the occurrence of the event. For example, when the predetermined time is 10 minutes, the control unit 460 controls the output unit 420 to count the 10 minutes based on the response time of the user and to output an event.

In addition, although the control unit 460 may maintain the current operation mode when the user is determined to be in the non-sleep state, the control unit 460 may reset a subsequent event generation period according to a kind of information inputted by the user. For example, when the operation mode is maintained, the control unit 460 may update a period of an event to be outputted in the subsequent period to a period corresponding to a kind of predetermined information inputted by the user.

In this case, the period corresponding to the kind of the predetermined information may be equal to or different from the predetermined period (e.g., 10 minutes). For example, when a voice signal is inputted by the user, it is possible to output the event of the subsequent period after 5 minutes, and when a vibration signal is inputted by the user, it is possible to output the event of the subsequent period after 10 minutes, and when a touch signal is inputted by the user, it is possible to output the event of the subsequent period after 15 minutes. Here, the period according to the kind of the inputted information may be set by the user through a setting unit (not shown).

When the control unit 460 determines that the user is in the sleep state, the control unit 460 switches the operation mode to the standby mode to transmit a control signal for managing the power supplied to the electrical appliances 200 to the power supply device 300.

Here, the control signal is power management information applied to the standby mode, and includes information for supplying or blocking power to each electrical appliances 200 or changing the supply level for each socket outlet of the power supply device 300. The control signal, that is, the power management information may be added, changed, or deleted by a user through a setting unit (not shown), and may be set to the same condition or different conditions for each socket outlet.

As described above, when the user is in the sleep state, the control unit 460 may transmit the control signal to the power supply device 300 to turn off at least one electrical appliance 200 currently connected to the power supply device 300 or to lower the power supply level, and it may maintain power supplied to some of the electrical appliances 200.

In addition, the control unit 460 may control a screen output of the display unit 450 to provide the user with the power supply state information of the electrical appliances 200 for each socket outlet received from the power supply device 300.

The communication unit 410 may wirelessly communicate with a separate user terminal. In this case, the control unit 460 may receive predetermined information from a user terminal through the communication unit 410 to provide it to the determination unit 440, and may provide the state information on the power supplied to the electrical appliances 200 to the user terminal.

The electrical appliance control device 400 according to the exemplary embodiment of the present invention may correspond to a user terminal such as a smart phone, a tablet PC, a PAD, and the like.

The electrical appliance control device 400 may be implemented as a program to operate in an electronic device such as a smart phone, a tablet PC, a PAD, and the like. Alternatively, the electrical appliance control device 400 may be implemented and operated as a single device that may perform each function.

Further, the functions included in the electrical appliance control device 400 may be modularized and embodied in the power supply device 300 or the electrical appliance 400.

As such, when the functions included in the electrical appliance control device 400 may be modularized and embodied, the electrical appliance control device 400 may be omitted in the system of FIG. 2. In this case, the power supply device 300 or the electrical appliance 400 may be connected to a separate user terminal (e.g., a smart phone) to operate by receiving information inputted from the user terminal.

When the functions of the electrical appliance control device 400 is modularized in the power supply device 300, the power supply device 300 may directly generates a predetermined event, and may control power supplied to at least one electrical appliance 200 based on predetermined information inputted in response to the event.

In addition, when the functions of the electrical appliance control device 400 is modularized in at least one electrical appliance 200, the electrical appliance 200 with the modularized functions may directly generate a predetermined event, and may control its own power and power supplied to the remaining appliances 200 based on predetermined information inputted in response to the event. In this case, when each electrical appliance 200 is connected to the user terminal, the electrical appliance 200 may provide the state information to the user terminal.

As such, according to the electrical appliance control system according to the exemplary embodiment of the present invention, it is possible to efficiently control the power supplied to the electrical appliance by determining the state of the user based on whether or not predetermined information is inputted from the user in response to the event outputted by the electrical appliance control device.

Therefore, even when the user is sleeping while reading, watching a movie, or listening to music, it is possible to save electricity by efficiently blocking the power supplied to the electrical appliance or lowering the level of the power.

Hereinafter, referring to FIG. 3, an electrical appliance control method using the electrical appliance control device according to the exemplary embodiment of the present invention will be described.

FIG. 3 illustrates a flowchart of an electrical appliance control method performed by the electrical appliance control device of FIG. 1.

As shown in FIG. 3, when the power supply device 300 according to the exemplary embodiment of the present invention is wirelessly connected to the electrical appliance control device 400, it transmits the power supply state information of at least one electrical appliance 200 corresponding to at least one socket outlet to the electrical appliance control device 400 (S310).

Then, the electrical appliance control device 400 may check the list of the electrical appliances 200 corresponding to each socket outlet and the power supply state of each electrical appliance 200 through the display unit 450. Here, the electrical appliance control device 400 may add, set, change, or delete power management information of each electrical appliance 200 applied to the standby mode through operation of the user on the list that is currently provided.

The output unit 420 of the electrical appliance control device 400 outputs a predetermined event at a predetermined period (e.g., 10 minutes) when the operation mode is executed (S320). Subsequently, the determination unit 440 determines whether predetermined information is inputted by the user within a predetermined time (e.g., 1 minute) corresponding to the predetermined event, and then provides the determined result to the control unit 460 (S330).

When the predetermined information is inputted within the predetermined time, the determination unit 440 determines that the user is in the non-sleep state, and the control unit 460 maintains the current operation mode corresponding to the non-sleep state.

However, in order to maintain the operation mode, the control unit 460 initializes the start counting time of the event generation period so that an event of a next period is outputted, and at the same time, the control unit 460 updates the event generation period corresponding to a kind of the predetermined information (e.g., voice, touch, and vibration information) (S340).

In addition, when the predetermined information is not inputted within the predetermined time, the determination unit 440 determines that the user is in the sleep state, and thus, the control unit 460 generates the control signal for blocking the power supplied to the electrical appliance 200 or for lowering the power to the predetermined level, and then transmits it to the power supply device 300 (S350).

When the power supply device 300 receives the control signal from the electrical appliance control device 400, the power supply device 300 blocks the power supplied to the electrical appliance 200 or lowers the power to the predetermined level according to the control signal (S360).

In the electrical appliance control method according to the exemplary embodiment of the present invention described above, the electrical appliance control device 400 is connected to one power supply device 300 to control the electrical appliance 200, but the electrical appliance control device 400 may simultaneously control a plurality of the power supply devices 300. Thus, the electrical appliance control device 400 may control the power supplied to the electrical appliances 200 connected to each of the plurality of the power supply device 300.

As such, according to the exemplary embodiment of the present invention, since it is possible to control the power supplied to the electrical appliance by determining the state of the user based on whether or not predetermined information is inputted from the user in response to the event outputted by the electrical appliance control device, even when the user is sleeping while reading, watching a movie, or listening to music, it is possible to efficiently block the power supplied to the electrical appliance or to lower the level of the power.

In addition, the user may sleep well enough without worrying about power-off of the electrical appliance and does not have to worry about the electric charge caused by operation of the electrical appliance during the sleeping time.

The accompanying drawings and the detailed description of the invention are only illustrative and are used for the purpose of describing the present invention, but those skilled in the art will understand that various modifications and other equivalent embodiments of the present invention are possible. Consequently, the true technical protective scope of the present invention must be determined based on the technical spirit of the appended claims.

The invention claimed is:

1. An electrical appliance control device for controlling power supplied to an electrical appliance, comprising a non-transitory computer-readable storage device, wherein a plurality of units are implemented in the storage device, the units comprising:

an output unit configured to output a predetermined event for each predetermined period while the electrical appliance is in an operation mode, wherein the predetermined event includes a first predetermined event and a second predetermined event which are selected from any one of a sound event, a vibration event, a light event, and a screen popup event;

an input unit configured to receive predetermined information in response to the predetermined event and to provide the predetermined information to the determination unit, wherein the predetermined information includes a first predetermined information and a second predetermined information which are selected from any one of sound information, vibration information, and touch information inputted by a user in response to the predetermined event;

a determination unit configured to determine a state of the user based on whether the predetermined information is inputted by the user; and a control unit configured to control power supplied to the electrical appliance corresponding to whether the predetermined information is inputted, wherein upon maintaining the operation mode, the control unit is configured to update a first time period of the first predetermined event based on the first predetermined information and to update a second distinctive time period of the second predetermined event from the first time period based on the second predetermined information.

2. The electrical appliance control device of claim 1, wherein
the control unit controls the power supplied to the electrical appliance by maintaining the operation mode or switching the operation mode to a standby mode corresponding to the state of the user.

3. The electrical appliance control device of claim 2, wherein
the determination unit determines that the user is in a non-sleep state when the predetermined information is inputted within a predetermined time from when the predetermined event is outputted, and
the determination unit determines that the user is in a sleep state when the predetermined information is not inputted within a predetermined time from when the predetermined event is outputted.

4. The electrical appliance control device of claim 3, wherein
when the user is in the non-sleep state, the control unit maintains the operation mode, and initializes a start counting time of the predetermined period.

5. The electrical appliance control device of claim 1, wherein the electrical appliance control device includes a communication unit communicating with a power supply device that manages the power supplied to the electrical appliance.

6. The electrical appliance control device of claim 5, wherein
the control unit transmits a control signal for controlling the power supplied to the electrical appliance to the power supply device through the communication unit.

7. The electrical appliance control device of claim 6, wherein
the power supply device includes at least one socket outlet that controls power supplied to at least one electrical appliance, and
the control signal includes information of maintaining or blocking the power supplied to the electrical appliance, or of changing a level of the power, which is power management information applied to the standby mode as a mode that is switchable in the operation mode corresponding to whether the predetermined information is inputted.

8. The electrical appliance control device of claim 7, further comprising:
a display unit that receives a list of the electrical appliances corresponding to a specific code of each socket outlet from the power supply device and state information of power supplied to the electrical appliances to display them on a screen.

9. The electrical appliance control device of claim 1, wherein
the electrical appliance control device includes a communication unit that wirelessly communicates with a user terminal, and
the control unit receives the predetermined information from the user terminal through the communication unit to provide it to the determination unit, and provides the state information of the power supplied to the electrical appliance to the user terminal.

10. An electrical appliance control method of using an electrical appliance control device for controlling power supplied to an electrical appliance, comprising:
outputting a predetermined event for each predetermined period while the electrical appliance is in an operation mode,
wherein the predetermined event includes a first predetermined event and a second predetermined event which are selected from any one of a sound event, a vibration event, a light event, and a screen popup event;
inputting predetermined information including a first predetermined information and a second predetermined information which are selected from any one of sound information, vibration information, and touch information inputted by a user in response to the predetermined event;
determining a state of the user based on whether predetermined information is inputted by the user; and
controlling, by a control unit, power supplied to the electrical appliance corresponding to whether the predetermined information is inputted,
wherein upon maintaining the operation mode, the control unit is configured to update a first time period of the first predetermined event based on the first predetermined information and to update a second distinctive time period of the second predetermined event from the first time period based on the second predetermined information.

11. The electrical appliance control method of claim 10, wherein
the controlling of the power supplied to the electrical appliance includes controlling the power supplied to the electrical appliance by maintaining the operation mode or switching the operation mode to a standby mode corresponding to the state of the user.

12. The electrical appliance control method of claim 11, wherein
the determining of whether predetermined information is inputted includes determining that the user is in a non-sleep state when the predetermined information is inputted within a predetermined time from when the predetermined event is outputted, and determining that the user is in a sleep state when the predetermined information is not inputted within a predetermined time from when the predetermined event is outputted.

13. The electrical appliance control method of claim 12, wherein
when the user is in the non-sleep state, the control unit maintains the operation mode, and initializes a start counting time of the predetermined period.

14. The electrical appliance control method of claim 10, wherein
the electrical appliance control device communicates with a power supply device that manages the power supplied to the electrical appliance.

15. The electrical appliance control method of claim 14, wherein
the controlling of the power supplied to the electrical appliance includes transmitting a control signal for controlling the power supplied to the electrical appliance to the power supply device.

16. The electrical appliance control method of claim 15, wherein
the power supply device includes at least one socket outlet that controls power supplied to at least one electrical appliance, and
the control signal includes information of maintaining or blocking the power supplied to the electrical appliance, or of changing a level of the power, which is power management information applied to the standby mode as a mode that is switchable in the operation mode corresponding to whether the predetermined information is inputted.

17. The electrical appliance control method of claim 16, further comprising:

receiving a list of the electrical appliances corresponding to a specific code of each socket outlet from the power supply device and state information of the power supplied to the electrical appliances to display them on a screen.

18. The electrical appliance control method of claim 10, wherein the electrical appliance control device wirelessly communicates with a user terminal, the controlling of the power supplied to the electrical appliance includes receiving the predetermined information from the user terminal and providing the state information of the power supplied to the electrical appliance to the user terminal.

\* \* \* \* \*